(12) United States Patent
Teo

(10) Patent No.: US 7,156,836 B2
(45) Date of Patent: Jan. 2, 2007

(54) CANNULA ASSEMBLY

(76) Inventor: Richard Keng Siang Teo, 108 Cactus Road, Singapore 809631 (SG)

(*) Notice: Subject to any disclaimer, the term of this patent is extended or adjusted under 35 U.S.C. 154(b) by 0 days.

(21) Appl. No.: 10/258,826

(22) PCT Filed: Apr. 19, 2001

(86) PCT No.: PCT/SG01/00068

§ 371 (c)(1),
(2), (4) Date: Oct. 25, 2002

(87) PCT Pub. No.: WO01/83006

PCT Pub. Date: Nov. 8, 2001

(65) Prior Publication Data

US 2003/0093058 A1    May 15, 2003

(30) Foreign Application Priority Data

Apr. 28, 2000   (SG)   ................ 200002344

(51) Int. Cl.
*A61M 31/00* (2006.01)

(52) U.S. Cl. ....................... 604/508; 604/264

(58) Field of Classification Search ................ 604/164, 604/165, 167, 168, 170, 171, 192, 48, 500, 604/507, 508, 509, 510, 168.01
See application file for complete search history.

(56) References Cited

U.S. PATENT DOCUMENTS

| 3,348,544 | A | * | 10/1967 | Braum | 604/164 |
| 3,388,703 | A | * | 6/1968 | Bowes | 604/166.01 |
| 3,454,006 | A | * | 7/1969 | Langdon | 604/164 |
| 3,565,074 | A | * | 2/1971 | Foti | 604/164.11 |
| 3,612,050 | A | * | 10/1971 | Sheridan | 604/166.01 |
| 3,714,945 | A | * | 2/1973 | Stanley | 128/214.4 |
| 3,825,001 | A | * | 7/1974 | Bennet et al. | 604/170.02 |
| 4,099,528 | A |   | 7/1978 | Sorenson et al. |   |
| 4,205,675 | A | * | 6/1980 | Vaillancourt | 604/508 |
| 4,250,881 | A |   | 2/1981 | Smith |   |
| 4,445,893 | A | * | 5/1984 | Bodicky | 604/165.04 |
| 4,488,545 | A | * | 12/1984 | Shen | 128/207.29 |
| 4,531,935 | A | * | 7/1985 | Berryessa | 604/45 |
| 4,588,398 | A | * | 5/1986 | Daugherty et al. | 604/265 |
| 4,828,549 | A | * | 5/1989 | Kvalo | 604/164 |
| 4,911,691 | A | * | 3/1990 | Aniuk et al. | 604/164 |
| 4,960,412 | A | * | 10/1990 | Fink | 604/167.04 |
| 4,964,854 | A | * | 10/1990 | Luther | 604/166.01 |
| 4,973,313 | A | * | 11/1990 | Katsaros et al. | 604/165.02 |
| 4,986,814 | A | * | 1/1991 | Burney et al. | 604/164.11 |
| 4,995,866 | A | * | 2/1991 | Amplatz et al. | 604/510 |
| 5,030,205 | A | * | 7/1991 | Holdaway et al. | 604/164 |
| 5,078,687 | A |   | 1/1992 | Egolf et al. |   |
| 5,156,596 | A |   | 10/1992 | Balbierz et al. |   |
| 5,533,988 | A | * | 7/1996 | Dickerson et al. | 604/280 |

(Continued)

FOREIGN PATENT DOCUMENTS

EP    0 186 256    7/1986

(Continued)

*Primary Examiner*—Manuel Mendez
(74) *Attorney, Agent, or Firm*—Baker & Daniels LLP

(57) ABSTRACT

A double cannula assembly for medical or veterinary use includes a first cannula (10) for insertion into a blood vessel in a conventional manner. This first cannula is an outer cannula and a second or inner cannula (12) is subsequently inserted through said first cannula to extend beyond the distal tip of the outer cannula. The inner cannula and outer cannula are formed to prevent blood entering between the engaging surfaces.

20 Claims, 5 Drawing Sheets

U.S. PATENT DOCUMENTS

| | | | |
|---|---|---|---|
| 5,618,272 A | * | 4/1997 | Nomura .................. 604/166.01 |
| 5,743,882 A | * | 4/1998 | Luther ........................ 604/168 |
| 5,817,060 A | * | 10/1998 | Overton et al. ............. 604/164 |
| 6,338,725 B1 | * | 1/2002 | Hermann et al. ........ 604/95.04 |

FOREIGN PATENT DOCUMENTS

| | | |
|---|---|---|
| EP | 0 417 764 | 3/1989 |
| EP | 0 955 070 | 11/1999 |
| JP | 10179734 | 7/1998 |

* cited by examiner

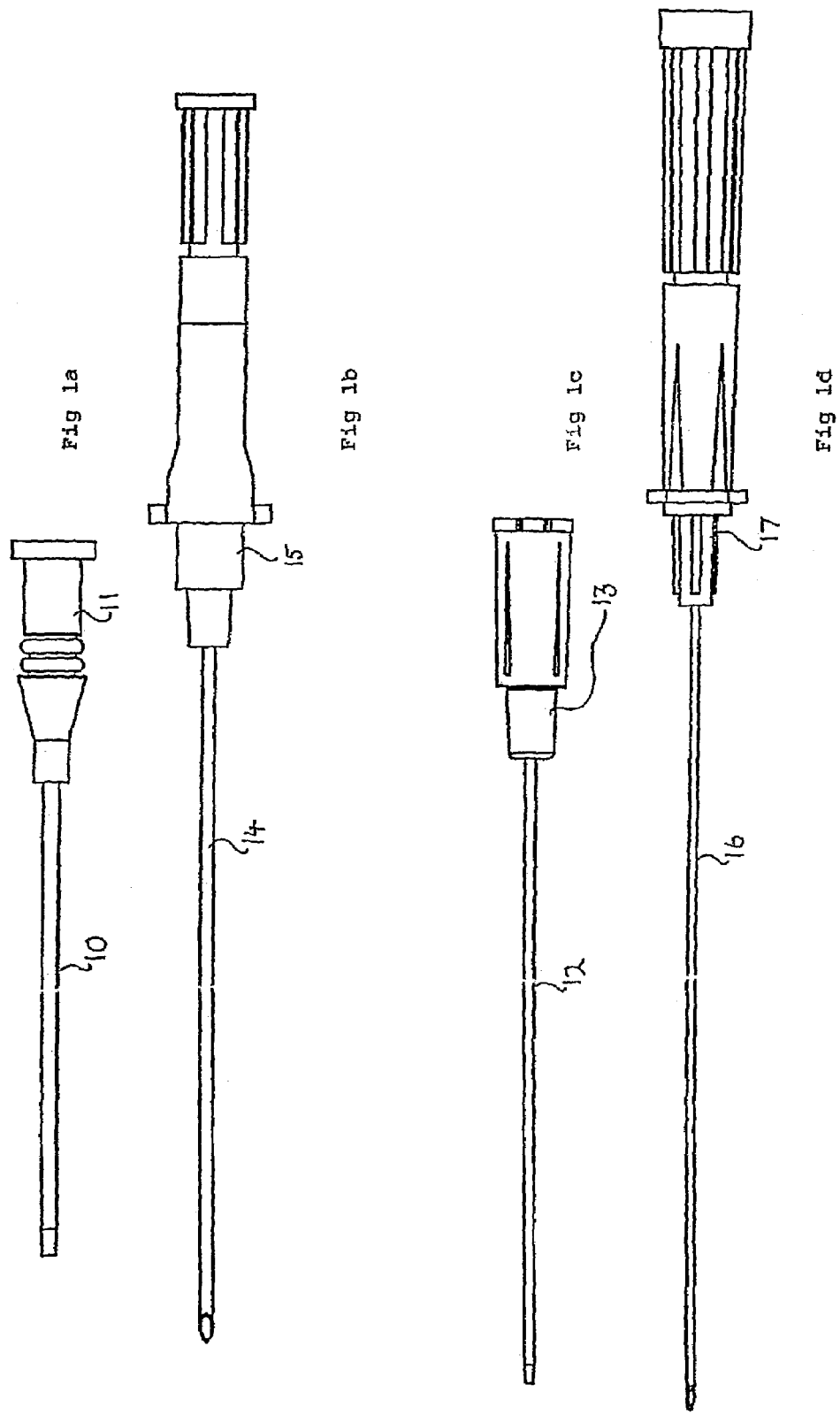

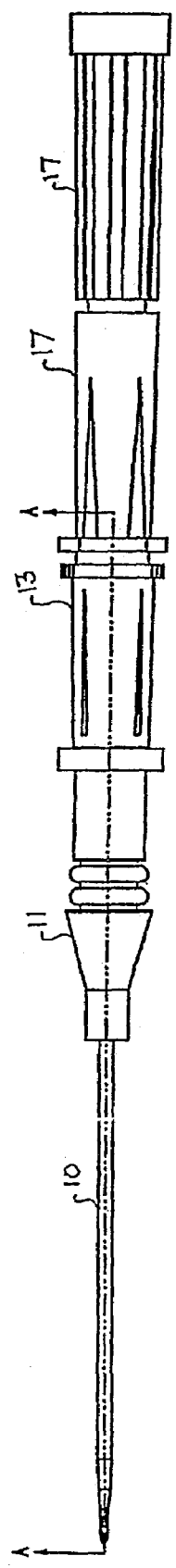
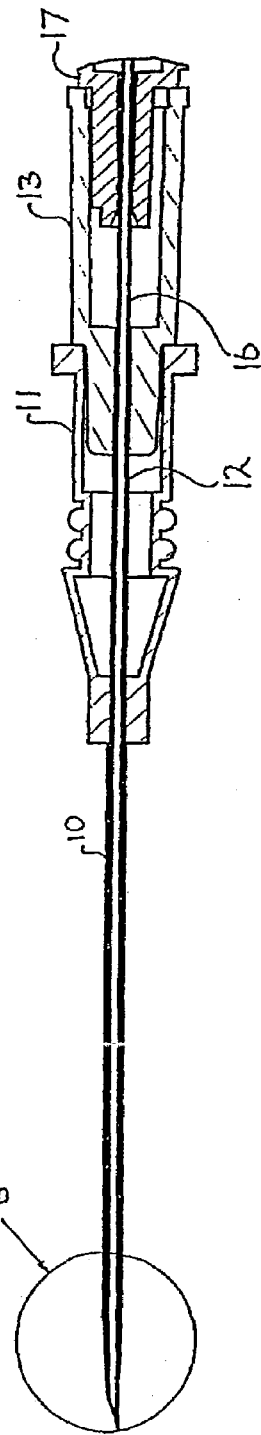
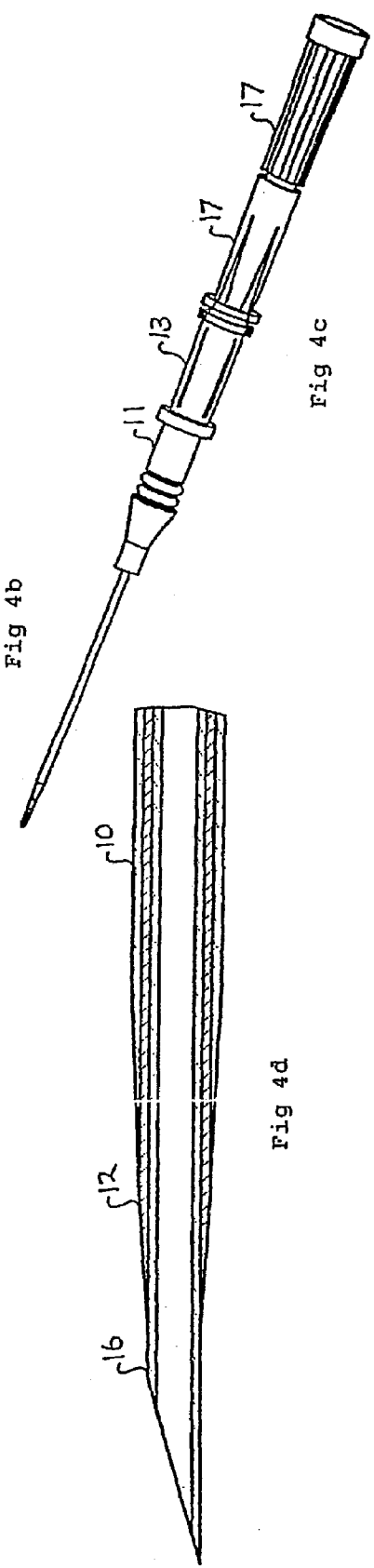
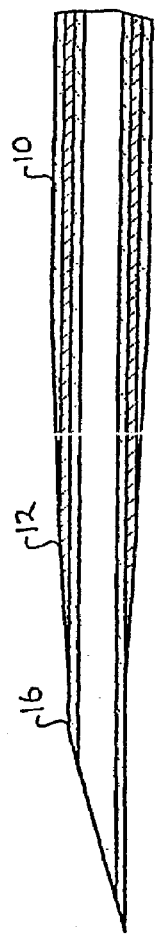
Fig 4a
Fig 4b
Fig 4c
Fig 4d

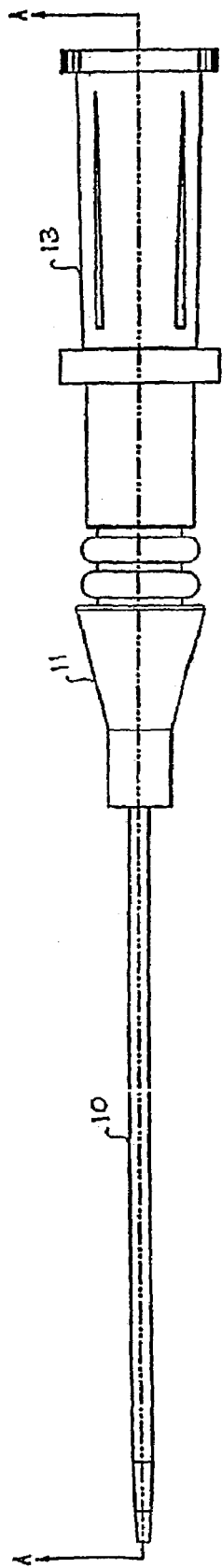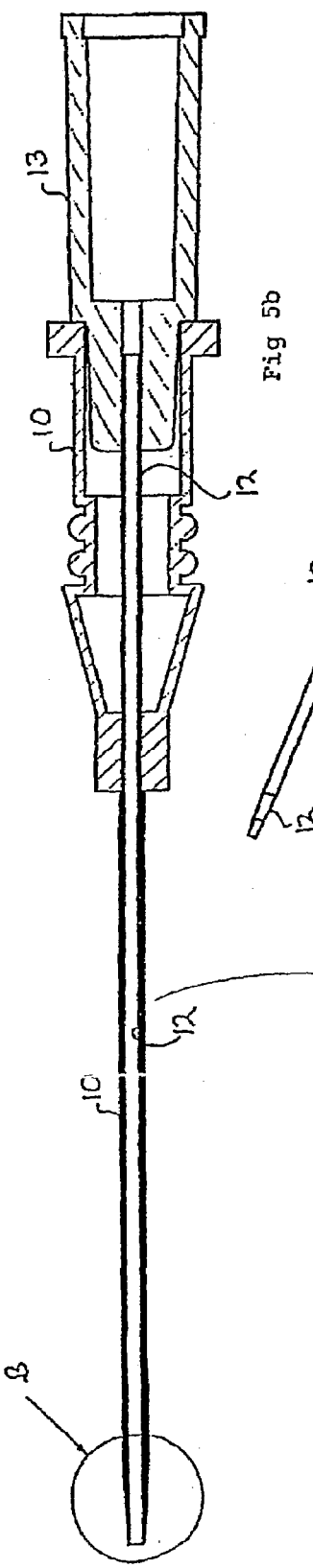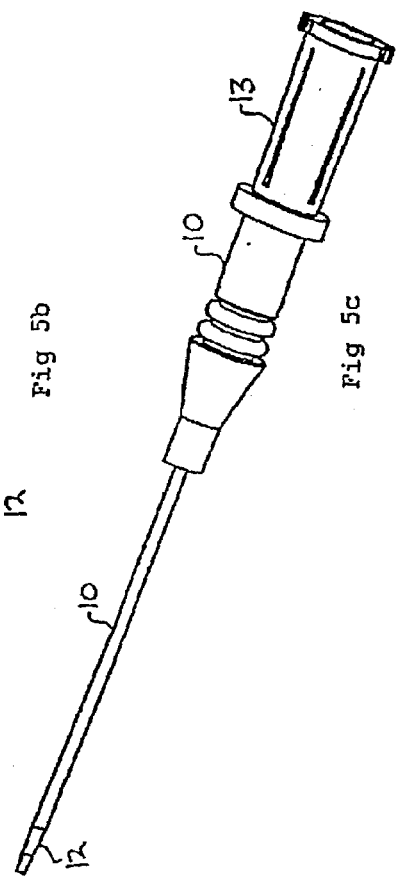
Fig 5a
Fig 5b
Fig 5c
Fig 5d

CANNULA ASSEMBLY

This application is the national phase under 35 U.S.C. § 371 of PCT International Application No. PCT/SG01/00068, which has an International filing date of Apr. 19, 2001 and designates the United States of America and which claims priority to Singapore Patent Application No. 200002344-0.

The present invention relates to a cannula assembly for medical use.

Current peripheral intravenous cannula tend to develop clots within the lumen of the cannula. This occurs when there is a back-flow of blood into the cannula (for example due to pressure difference in the veins and the cannula, after completing introduction of the intra-venous fluids). Unfortunately and more frequently than not, medical staff are not able to introduce heparinised saline (a chemical to reduce the incidence of clotting) into the cannula in time. Furthermore, factors such as the small size of the lumen of the cannula and the nature of the fluids and medication introduced, contributes to thrombus formation (clots). Not infrequently, patients do not receive their medication, fluids and chemotherapy on time because the intern on-duty, overwhelmed by workload, is unable to set a cannula site on time. Depending on the availability of the intern, it has been documented that some patients receive their medication some twelve hours later than the specified time.

Such indwelling cannula with stagnated and clotted blood within the lumen are a potential source of infection. The current widespread practice of "flushing the cannula" (using a water filled syringe, whereby the water is injected into the cannula to dislodge the clot) by the nursing staff and interns is done in order to avoid the need to restart a new cannula site. Dislodging the clot in the cannulas and introducing it into the blood stream can lead to septicemia and micro embolism. This is ethically wrong.

The frequent need for withdrawing blood and setting a new cannula site (for example due to clotting of cannula) is deemed the greatest source of discomfort in semi-well patients in hospitals (especially pediatrics and those of female gender with ill-defined veins, resulting in multiple attempts at blood sampling and setting cannula). This has been cited by many patients as one of the reasons why they are reluctant to be admitted to hospital. Furthermore, a third of the workload of the intern is spent on such procedures in hospitals in some parts of the world whereas this time could have been used to acquire more in-depth knowledge of managing patients. The nursing staff would be able to perform their task more efficiently if they did not have to await for the new cannula to be inserted by the doctor or phlebotomist.

At present, when the cannula gets obstructed by clots/thrombus, there are a few common but sub-optimal solutions. As mentioned above, medical staff attempt to dislodge the obstruction by flushing the cannula, for example, with water, normal saline or heparinised saline. A syringe is attached to the proximal end of the cannula and the fluid in the syringe is forced into the cannula so as to dislodge the clot/thrombus out of the cannula and into the patient's circulation. This is ethically wrong as it causes pain and introduces infection and micro-embolism.

Attempts have been made to remove the thrombus by suction technique. A syringe is attached to the proximal end of the cannula and the plunger is withdrawn to suck out the thrombus. However, the distal vein tends to collapse and thus makes such a technique impractical as the thrombus almost never gets removed.

In recent years, some companies have introduced new materials for manufacturing the cannula. The claim is that such materials (e.g. polyurethane) are able to reduce the rate of phlebitis (inflammation of the veins are due to various factors, which include clot formation and infection). However, the incidence of phlebitis is still high and the new product does not address the issues of thrombus formation nor does it permit multiple blood sampling attempts.

Attempts have been made by medical staff to introduce heparinised saline into the cannula after every procedure via the cannula. Heparin helps to prevent clot formation. However such an attempt is very operator dependent and requires strict discipline. Furthermore, there is frequent back-flow of blood into the cannula after completion of medication and fluids due to pressure difference. The nurse is generally unable to watch for the completion of every packet of fluid and thus when the back-flow of blood has occurred before the nurse attends to the problem, the cannula becomes obstructed.

Under current procedures, patients get multiple needle pricks at the hands, forearm and elbow for blood sampling throughout a stay in hospital. No known significant attempts have been made known to reduce the incidence of such a process. Catheters for larger vessels (e.g. Vena Cava) and arteries are available for withdrawing blood. Peripheral cannula for multiple blood withdrawing attempts are not available. This is because the lumen of the cannula tends to be obstructed by thrombus formation and the surfaces of the lumen are contaminated with the fluids and the medication introduced. Blood sampling from such a site will not be accurate. Furthermore, if blood has to be taken form such a site, the initial 3 to 5 mls of blood has to be discarded as it may contain Heparin or other substance that would invalidate the subsequent laboratory's blood investigation results.

It is an object of this invention to provide an intravenous cannula assembly which overcomes or avoids the aforementioned problems of existing devices or at least provides a useful alternative.

Accordingly, the invention provides a cannula assembly comprising an outer cannula and a separate inner cannula receivable within said outer cannula to form a liquid seal therewith.

In a further form the invention provides a method for intravenous fluid transfer with a patient, said method comprising the steps of inserting and securing a first cannula in a blood vessel, preventing back-flow of blood into said cannula, and inserting an inner cannula which is longer than said first cannula into, and through, said first cannula, said intravenuous fluid transfer taking place through the inner cannula.

An embodiment of the invention will now be described by way of example with reference to the accompanying drawings in which:

FIG. 1 shows the separate components of the embodiment of the cannula assembly to be described with FIGS. 1a and 1b showing respectively, an outer cannula and introducer and FIGS. 1c and 1d showing an inner cannula and introducer;

FIG. 4 shows the inner cannula and introducer inserted within the outer cannula and FIG. 4a is a side view showing the combination of the components of FIGS. 1a, 1c and 1d, FIG. 4b is a cross sectional view across A—A of FIG. 4a, FIG. 4c is a perspective view similar to FIG. 4a and FIG. 4d is an enlarged cross sectional view of region B of FIG. 4b;

FIG. 5 shows the inner cannula inserted within the outer cannula and FIG. 5a is a side view of the combination of a cannula of FIGS. 1a and 1c, FIG. 5b is a cross sectional view across A—A of FIG. 5a, FIG. 5c is a perspective view similar to FIG. 5a and FIG. 5d is an enlarged cross sectional view of region B of FIG. 5b.

Figure 2A:
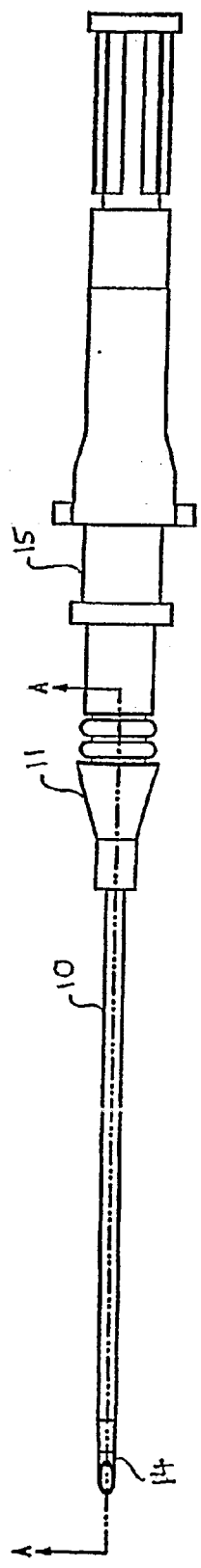
FIG. 2 shows the outer cannula assembly and FIG. 2a is a view similar to FIGS. 1a and 1b showing the introducer inserted in the outer cannula.

In the drawings an outer cannula 10 and inner cannula 12 are shown. The outer cannula 10 has a needle hub 11 at its proximal end and is shorter and has a larger diameter than inner cannula 12. The inner cannula 12 has a needle hub 13 at its proximal end and the outer diameter of the inner cannula 12 is a sliding fit within the inner diameter of the outer cannula 10. It is desirable that the inner cannula is a relatively tight sliding fit within the outer cannula 10 so as to prevent fluids entering between the two sliding surfaces. In other words, there is minimal clearance between the outer surface of the inner cannula and the inner surface of the outer cannula. Of course there must be sufficient clearing to allow relative sliding movement. The needle hub 11 is adapted to receive the needle hub 13 to hold the cannula together once the inner cannula has been inserted in the outer cannula as described below.

Figure 2B:
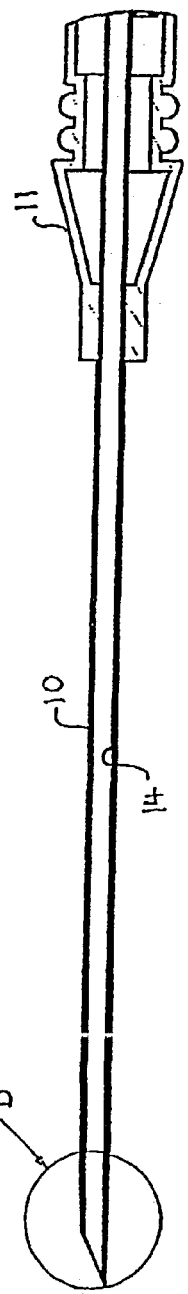
FIG. 2b is a cross-sectional view across A—A of FIG. 2a, FIG. 2c is a perspective view similar to FIG. 2a and FIG. 2d is an enlarged cross-sectional view of region B of FIG. 2b.
Figure 2C:
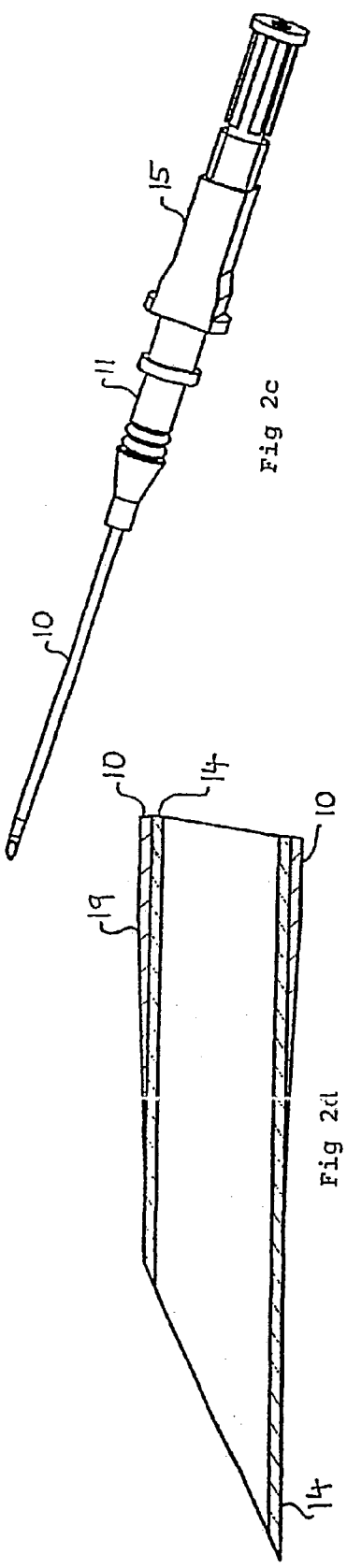
Figure 3A:
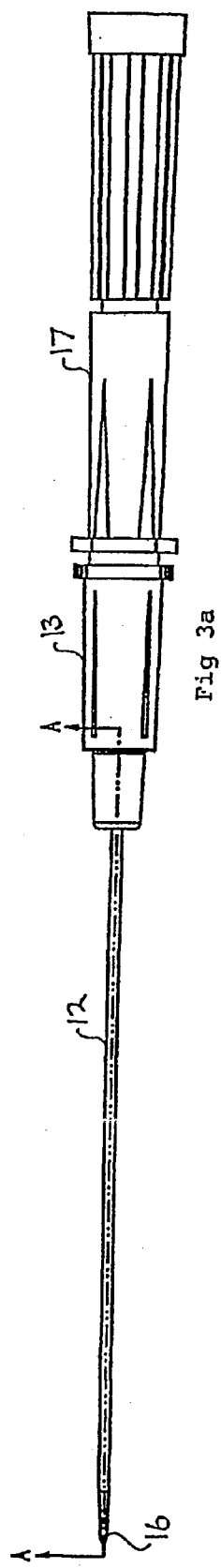
FIG. 3 shows the inner cannula and introducer and FIG. 3a is a view similar to FIGS. 1c and 1d showing the introducer inserted into the inner cannula.
Figure 3B:
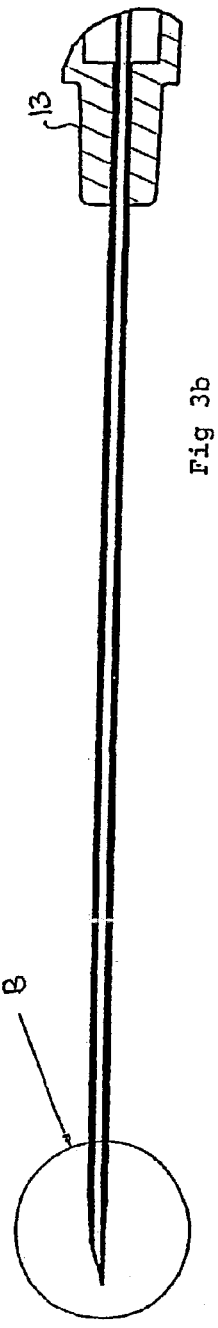
FIG. 3b is a cross-sectional view across A—A of FIG. 3a, FIG. 3c is a perspective view similar to FIG. 3a and FIG. 3d is an enlarged cross sectional view of region B of FIG. 3b.
Figure 3C:
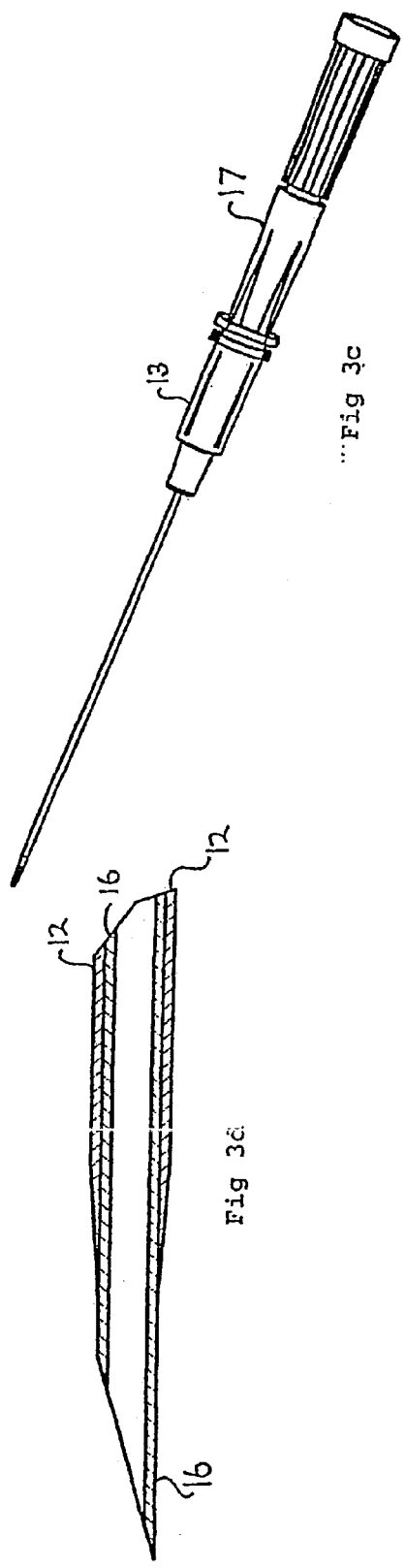
Figure 3D:
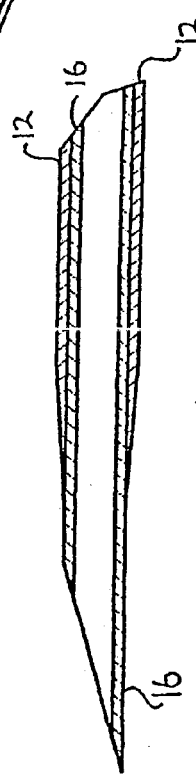

A first cannula introducer 14 in the form of a catheter/stylet needle is slightly longer than the outer cannula 10 and has a needle hub 15 that fits within the cannula hub 11 of the outer cannula 10 as is shown in FIGS. 2a–2c. Similarly a second cannula introducer 16 has a needle hub 17 that fits into the cannula hub 13 of the inner cannula 12 as shown in FIGS. 3a–3c. In each case the catheter needle passes through the respective cannula and extends a short distance past the distal end thereof for the purpose of inserting the cannula into the vein of a patient.

Figure 2D:
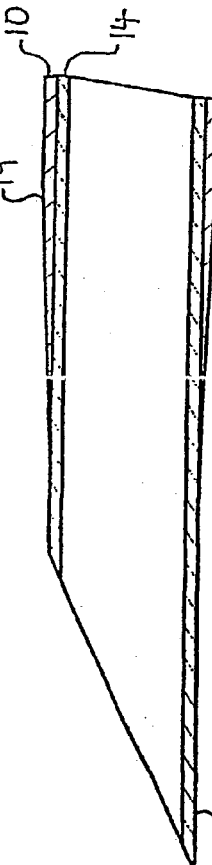

The distal tip of the outer cannula 10 is tapered at 19 (see FIG. 2d) and is preferably designed to exert a force on the outer surface of the inner cannula 12. This force may be achieved by having a slight reduction of the inner diameter of the cannula 10 at its distal end. Alternatively, the distal end may be collapsible (e.g. by being elastomeric) so that it exerts a resilient pressure on the inner cannula. As mentioned previously the contacting surfaces between the two cannula are a sliding tight fit which is sufficient to allow sliding movement between the two cannula but tight enough to prevent blood or other fluids from seeping in between the two surfaces (as shown in FIG. 5d). The inner cannula should fit into the outer cannula in a secure fashion such that it does not slip off accidentally. However, it should also be easily removable when intended without traumatising the vessels involved. The length of the inner cannula 12 is such that when the cannula hub 13 is engaged within the cannula hub 11 to hold the cannula together, the inner cannula 12 extending a short distance beyond the distal end of the outer cannula 10.

It should be mentioned that the cannula described above can be essentially the same as conventional cannula with the exception that the length and diameter of each are arranged such that one cannula is a sliding tight fit within the other cannula and preferably the outer cannula at its distal tip exerts a force on the outer surface of the inner cannula.

Having described the dual cannula of the present invention the method or procedure in using same will now be described.

In order to administer fluids (drugs and the like) to a patient using the described embodiment, firstly, the outer cannula 10 is inserted into the vein of a patient's hand, forearm or elbow in a typical fashion. This involves inserting the first cannula introducer 14 through the lumen of the outer cannula 10 so that the distal end of the introducer 14 extends slightly beyond the distal end of the cannula 10 for making a suitable incision to accommodate the cannula as shown in FIGS. 2a–2d. Once the outer cannula 10 is properly inserted and secured in the vein of a patient, the introducer 14 is withdrawn. The outer cannula 10 remains in the vein as is conventionally the case. Previously this cannula has been used mainly for daily medication or fluid infusion. However, this single cannula would clot easily and would normally be removed prematurely due to clotting/infection/phlebitis. If this was the end of the procedure, medical staff would flush the cannula to dislodge the clot as has been done in the past or replace the cannula.

However, with the double catheter assembly of the described embodiment of the present invention the next step is to apply pressure distal to the tip of the cannula 10 to prevent back-flow of blood into the cannula 10. This is usually done using the index finger. At this point the smaller and longer cannula 12 with its accompanying introducer 16 inserted as shown in FIGS. 3a-3d is subsequently inserted into the larger and shorter outer cannula 10 that is already in the patient's vein as illustrated in FIGS. 4a–4d (without showing the vein). The extra length of the inner cannula 12 allows its associated introducer 16 to extend further into the patient's vein enabling the distal end of the cannula 12 to be properly inserted therein. The introducer 16 is then withdrawn leaving the longer thinner cannula 12 within the shorter larger outer cannula 10. The arrangement is then as shown in FIGS. 5a–5d.

When the problem of clotting occurs or infection builds up within the lumen of the inner cannula 12 or when there is a need for blood sampling, the inner cannula 12 is removed. This leaves the outer cannula 10 in place. A new inner cannula 12 is then inserted through the outer cannula 10 and into the patient's vein in the same manner as occurred originally. Obviously the surface of the new inner cannula 12 is not contaminated. Thus it will not adversely affect the values of blood sampling, unlike the prior art where the inner cannula is contaminated on its inner surface by electrolytes, fluids and antibiotics which have been introduced into the patient.

The patient's vein distal to the cannula may have a reduced blood flow rate due to the proximal occupancy of the cannula and this may result in a partially collapsed vein. Thus a syringe of water (2 to 3 mls) can be introduced to assist in opening up the distal vein further when necessary. Subsequently, the first 2 to 3 mls of blood extracted from the patient will be discarded and the subsequent volume of blood is used for blood sampling. The outer cannula can be used as a normal cannula instead of functioning as a sheath on special occasions, for example, when there is a need for a slightly bigger lumen at emergency or in urgent situations.

It should be evident from the above that the assembly of the described embodiment provides apparatus whereby patients need only to have one, or minimal, veni-punctures during an entire stay in hospital. A typical patient will have the cannula inserted at the outset, for example, at the accident and emergency location. Subsequently, the inner cannula is changed according to different procedures, for example, fluid infusion, medications, blood sampling, without having to prick the patient multiple times. The inner cannula is easily renewed and the nursing staff can perform the necessary procedure. The invention avoids the practice of "flushing" the cannula, which causes pain, and introduces emboli and infection into the vascular system. The device of the present invention helps in reducing the colonisation of infective organisms as the inner cannula is constantly renewed. The apparatus is minimally operator dependent. In the prior art, nursing staff are required to look out constantly for the completion of intravenous fluid before the back-flow of blood occurs. Doctors or nurses injecting the fluid are required to be strict in discipline to inject heparinised saline into the cannula after every single procedure. The medical staff are required to constantly flush the cannula to keep it patent. With the described embodiment, the cannula is more "forgiving" in the sense that it allows more room for error whereby even if the medical staff could not flush the cannula with heparinised saline or remove the bag of intravenous fluid in time, the inner cannula can be changed accordingly and without having to prick the patient. Multiple daily blood sampling can be performed without the risk of contamination by the inner surface of the inner cannula as it renewed accordingly. This substantially reduces the number of needle pricks on a patient. Such an arrangement is particularly applicable for use with patients having fatal diseases such as HIV infection which can be transmitted through blood contact and for which a reduction in the number of needle insertions made by the nursing staff lead to a consequent reduction in the possibility of infection.

The embodiments are not to be construed as limitative. For example, although the first cannula has been illustrated having a sliding fit on the second cannula to prevent fluid entering between the two cannula, this need not be so, provided some means is used for preventing flow of fluid between the cannula. For example, the outer cannula may, at the tip only, be a sliding fit on the inner cannula, for example by making the outer cannula at its tip collapsible or reducing the inner diameter at the tip. Alternatively, the outer cannula may be internally collapsible over its whole length to form a seal, except when the inner cannular is inserted. Although the introducer for the inner cannula has been shown having a sharp point, this need not be sharp, since the insertion through the skin and vein of a patient has already been made by the outer cannula introducer. Providing the inner cannula introducer with a blunt end reduces the risk of needle injuries and consequent transfer of infection. Furthermore, although in many applications the inner cannula needs to project through the outer cannula, in some applications this need not occur, for example when there is a continuous injection or flow of fluid into the patient.

A variation where the inner cannula is replaced with a solid stopper is also envisaged. Such a stopper may completely replace the inner cannula, with the outer cannula being used for transfer of liquid to/from the patient or, alternatively, may be swopped with the inner cannula where no flow of fluid in or out of the patient is desired.

Furthermore, the inner and/or outer cannula may be provided with a one way valve, to prevent ingress or egress of fluid, depending upon use.

The invention claimed is:

1. A method of intravenous connection to a human subject, said method comprising the steps of:
   inserting and securing a flexible outer peripheral venous catheter in a vein;
   inserting a flexible first inner peripheral venous catheter which is thinner than said outer catheter into and through said outer catheter so that an intravenous connection takes place through the first inner catheter;
   selectively removing the first inner catheter from the outer catheter while the outer catheter remains in the vein; and
   inserting a flexible second inner peripheral venous catheter substantially identical to the first inner catheter into and through said outer catheter so that the intravenous connection takes place through the second inner catheter, wherein the first inner catheter is replaced with the second inner catheter from time to time when a lumen of the first inner catheter is clotted or to reduce the chance of an infection building up in said lumen.

2. The method of claim 1, further comprising the step of preventing back-flow of blood into said outer catheter prior to inserting the first and second catheters into and through the outer catheter.

3. The method of claim 1, wherein the inner and outer catheters are inserted using an introducer which extends beyond a distal tip of the inner and outer catheters and is withdrawn after insertion of the inner and outer catheters.

4. The method of claim 1, wherein the first and second inner catheters each have first and second opposing ends defining a lumen therebetween, both the first and second ends being open for infusion of liquid to the vein and for withdrawing blood from the vein from one end to the other end.

5. The method of claim 4, wherein the outer catheter has first and second opposing ends defining a lumen therebetween for receiving the inner catheter therein, both the first and second ends of the outer catheter being open for infusion of liquid to the vein and for withdrawing blood from the vein from one end to the other end.

6. The method of claim 1, wherein the inner and outer catheters are formed of a plastic material.

7. The method of claim 1, wherein the step of inserting and securing the outer catheter in the vein includes using a first introducer which extends beyond a distal tip of the outer catheter for inserting the outer catheter into the vein, whereby the outer catheter is arranged to indwell in said vein upon withdrawal of the first introducer.

8. The method of claim 7, wherein the step of inserting the first and second inner catheters into and through the outer catheter includes using a second introducer which extends beyond a distal tip of the first and second inner catheters for separately inserting the first and second inner catheters into and through the outer catheter, whereby the first and second inner catheters are separately arranged to indwell in outer catheter upon withdrawal of the second introducer from the first and second inner catheters.

9. The method of claim 1, wherein the step of inserting the first and second inner catheters into and through the outer catheter includes using a second introducer which extends beyond a distal tip of the first and second inner catheters for separately inserting the first and second inner catheters into and through the outer catheter, whereby the first and second inner catheters are separately arranged to indwell in outer catheter upon withdrawal of the second introducer from the first and second inner catheters.

10. The method of claim 1, wherein the step of inserting the first inner catheter into and through the outer catheter occurs after the step of inserting and securing an outer catheter in a peripheral vein.

11. A method of intravenous connection to a human subject, said method comprising the steps of:

inserting and securing a flexible outer catheter in a vein;

inserting a flexible first inner catheter which is thinner than said outer catheter into and through said outer catheter so that an intravenous connection takes place through the first inner catheter;

selectively removing the first inner catheter from the outer catheter while the outer catheter remains in the vein; and inserting a flexible second inner catheter substantially identical to the first inner catheter into and through said outer catheter so that the intravenous connection takes place through the second inner catheter, wherein the outer catheter has a reduced inner diameter to exert pressure on the first and second inner catheters passing therethrough.

12. The method of claim 11, wherein the flexible outer catheter is a peripheral venous catheter, the first inner catheter is a peripheral venous catheter, and the second inner catheter is a peripheral venous catheter.

13. A peripheral intravenous catheter assembly for indwelling in a vein, the catheter assembly comprising:

a flexible outer peripheral venous catheter being formed of plastic material and having first and second opposing ends defining a lumen therebetween, both the first and second ends of the outer catheter being open, the outer catheter being arranged to be inserted into and secured within a vein; and a flexible first inner peripheral venous catheter being formed of plastic material and having first and second opposing ends defining a lumen therebetween, both the first and second ends of the first inner catheter being open, the first inner catheter being positioned within said outer catheter to form a liquid seal therewith for infusion of liquid to the vein and for withdrawing blood from the vein from one end to the other end through the lumen of the first inner catheter, the inner and outer catheters being arranged to indwell in said vein and the first inner catheter being replaceable with a second inner peripheral venous catheter, substantially identical to the first inner catheter, from time to time when the lumen of the first inner catheter is clotted or when infection builds up in said lumen.

14. The assembly of claim 13, further comprising a first introducer configured to extend through the lumen of the outer catheter and beyond a distal tip of the outer catheter for inserting the outer catheter into the vein, whereby the outer catheter is arranged to indwell in said vein upon withdrawal of the first introducer.

15. The assembly of claim 14, further comprising a second introducer configured to extend through the lumen of either of the first and second inner catheters and beyond a distal tip of first and second inner catheters for separately inserting the first and second inner catheters into and through the outer catheter, whereby the first and second inner catheters are separately arranged to indwell in outer catheter upon withdrawal of the second introducer from the first and second inner catheters.

16. The assembly of claim 13, wherein the outer catheter has a reduced inner diameter to exert pressure on the first and second inner catheters passing therethrough.

17. The assembly of claim 13, wherein the first and second inner catheters each have a sliding fit within said outer catheter to form a seal between the first and second inner catheters and the outer catheter.

18. The assembly of claim 13, wherein a distal end of said outer catheter exerts pressure on an outer surface of the first and second inner catheters passing therethrough.

19. The assembly of claim 18, wherein the flexible outer catheter is a peripheral venous catheter, the first inner catheter is a peripheral venous catheter, and the second inner catheter is a peripheral venous catheter.

20. The assembly of claim 13, wherein the outer catheter is internally collapsible when the first and second inner catheters are not inserted in the outer catheter.

* * * * *